(12) United States Patent
Zhang et al.

(10) Patent No.: US 9,975,121 B2
(45) Date of Patent: *May 22, 2018

(54) MICROFLUIDIC DEVICES, SYSTEMS, AND METHODS FOR EVALUATING TISSUE SAMPLES

(71) Applicant: UNIVERSITY OF NOTRE DAME, Notre Dame, IN (US)

(72) Inventors: Siyuan Zhang, Granger, IN (US); Jeremiah Zartman, Granger, IN (US); David Hoelzle, South Bend, IN (US); Cody Narciso, Mishawaka, IN (US)

(73) Assignee: University of Notre Dame, Notre Dame, IN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/738,335

(22) Filed: Jun. 12, 2015

(65) Prior Publication Data
US 2015/0360224 A1 Dec. 17, 2015

Related U.S. Application Data

(60) Provisional application No. 62/011,146, filed on Jun. 12, 2014, provisional application No. 62/138,043, filed on Mar. 25, 2015.

(51) Int. Cl.
*B01L 3/00* (2006.01)
*C12M 3/06* (2006.01)

(52) U.S. Cl.
CPC ....... *B01L 3/502715* (2013.01); *C12M 23/16* (2013.01); *B01L 2200/025* (2013.01);
(Continued)

(58) Field of Classification Search
CPC ....... B01L 3/502715; B01L 2300/0645; B01L 2300/123; B01L 2300/06;
(Continued)

(56) References Cited

U.S. PATENT DOCUMENTS 6,645,759 B2 * 11/2003 Banes .................... C12M 35/04
435/293.1
6,875,619 B2 * 4/2005 Blackburn ........... B01J 19/0093
435/287.1
(Continued)

OTHER PUBLICATIONS

Burnette, Miranda, et al. "An inverse small molecule screen to design a chemically defined medium supporting long-term growth of *Drosophila* cell lines." Molecular BioSystems 10.10 (2014): 2713-2723.
(Continued)

*Primary Examiner* — Gautam Prakash
(74) *Attorney, Agent, or Firm* — Tarolli, Sundheim, Covell & Tummino LLP

(57) ABSTRACT

A microfluidic device for evaluating a tissue sample can include a tissue chamber, a liquid inlet channel, a liquid outlet channel, and at least one of components (1)-(3). The tissue chamber can be defined by a plurality of walls, at least one of which is transparent. The liquid inlet and outlet channels can be in fluid communication with the tissue chamber. Components (1)-(3) can include: (1) a deformable membrane disposed within the tissue chamber and being configured to oscillate, upon application of pressure thereto, to mechanically compress the tissue sample; (2) first and second electrodes disposed about the tissue chamber and being configured such that delivery of electrical energy thereto creates an electrical gradient across the tissue chamber; and (3) at least one deformable wall, which partially defines the tissue chamber and is configured to stretch either uniaxially or biaxially upon application of negative pressure to the tissue chamber.

10 Claims, 20 Drawing Sheets

(52) U.S. Cl.
CPC . *B01L 2200/028* (2013.01); *B01L 2200/0647* (2013.01); *B01L 2200/143* (2013.01); *B01L 2300/023* (2013.01); *B01L 2300/044* (2013.01); *B01L 2300/06* (2013.01); *B01L 2300/0645* (2013.01); *B01L 2300/123* (2013.01); *B01L 2400/0439* (2013.01); *B01L 2400/0481* (2013.01); *B01L 2400/0487* (2013.01)

(58) Field of Classification Search
CPC ....... B01L 2400/0439; B01L 2200/028; B01L 2400/0487; B01L 2200/025; B01L 2200/0647; B01L 2200/143; B01L 2300/023; B01L 2300/044; B01L 2400/0481; C12M 23/16
See application file for complete search history.

(56) References Cited

U.S. PATENT DOCUMENTS

| | | | | |
|---|---|---|---|---|
| 2006/0019379 | A1* | 1/2006 | Taylor et al. .......... | C12M 47/06 435/306.1 |
| 2010/0041128 | A1* | 2/2010 | Banes et al. .......... | C12M 23/16 435/287.9 |

OTHER PUBLICATIONS

Campàs, Otger, et al. "Quantifying cell-generated mechanical forces within living embryonic tissues." Nature methods 11.2 (2014): 183-189.

Chen, Tsai-Wen, et al. "Ultrasensitive fluorescent proteins for imaging neuronal activity." Nature 499.7458 (2013): 295-300.

Cheung, Lily S., and Stanislav Shvartsman. "A Multiplex Fluorescent in Situ Hybridization Protocol for Clonal Analysis of *Drosophila* Oogenesis." Tissue Morphogenesis. Springer New York, 2015. 115-122.

Elliott, David A., and Andrea H. Brand. "The GAL4 system." *Drosophila*. Humana Press, 2008. 79-95.

Frampton, John P., et al. "Aqueous two-phase system-mediated antibody micropatterning enables multiplexed immunostaining of cell monolayers and tissues." Biotechnology journal 10.1 (2015): 121-125.

Han, Zhou, et al. "Fluorescent protein voltage probes derived from ArcLight that respond to membrane voltage changes with fast kinetics." PLOS One 8(11) (2013): e81295.

Huang, Juan, et al. "Directed, efficient, and versatile modifications of the *Drosophila* genome by genomic engineering." Proceedings of the National Academy of Sciences 106.20 (2009): 8284-8289.

Issadore, David, et al. "Microwave dielectric heating of drops in microfluidic devices." Lab on a Chip 9.12 (2009): 1701-1706.

Krüger, Julia, and Johannes Bohrmann. "Bioelectric patterning during oogenesis: stage-specific distribution of membrane potentials, intracellular pH and ion-transport mechanisms in *Drosophila* ovarian follicles." BMC developmental biology 1 (2015): 1.

Stott, Shannon L., et al. "Isolation of circulating tumor cells using a microvortex-generating herringbone-chip." Proceedings of the National Academy of Sciences 107.43 (2010): 18392-18397.

Yazdi, Shahrzad, and Arezoo M. Ardekani. "Bacterial aggregation and biofilm formation in a vortical flow." Biomicrofluidics 6.4 (2012): 044114.

Zartman, Jeremiah, Simon Restrepo, and Konrad Basler. "A high-throughput template for optimizing *Drosophila* organ culture with response-surface methods." Development 140.3 (2013): 667-674.

\* cited by examiner

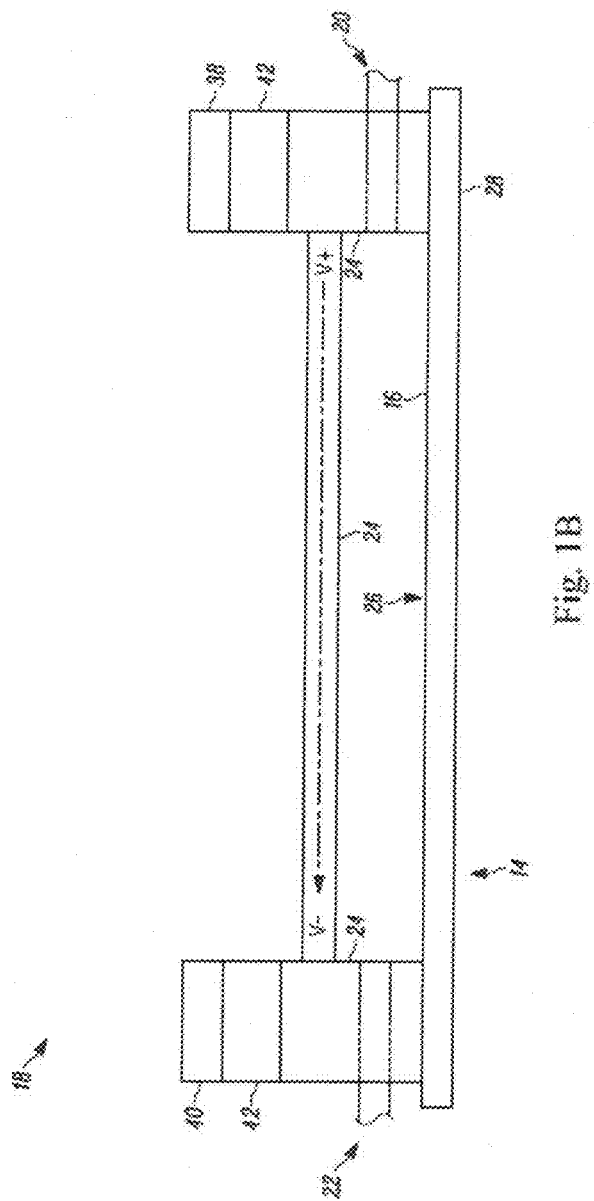

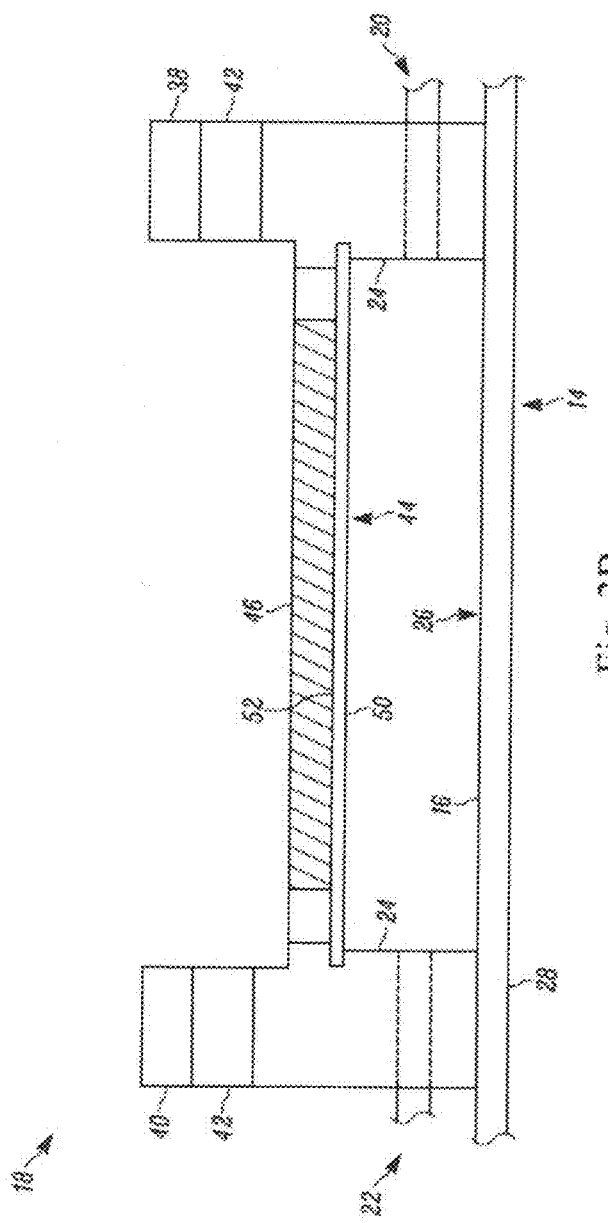

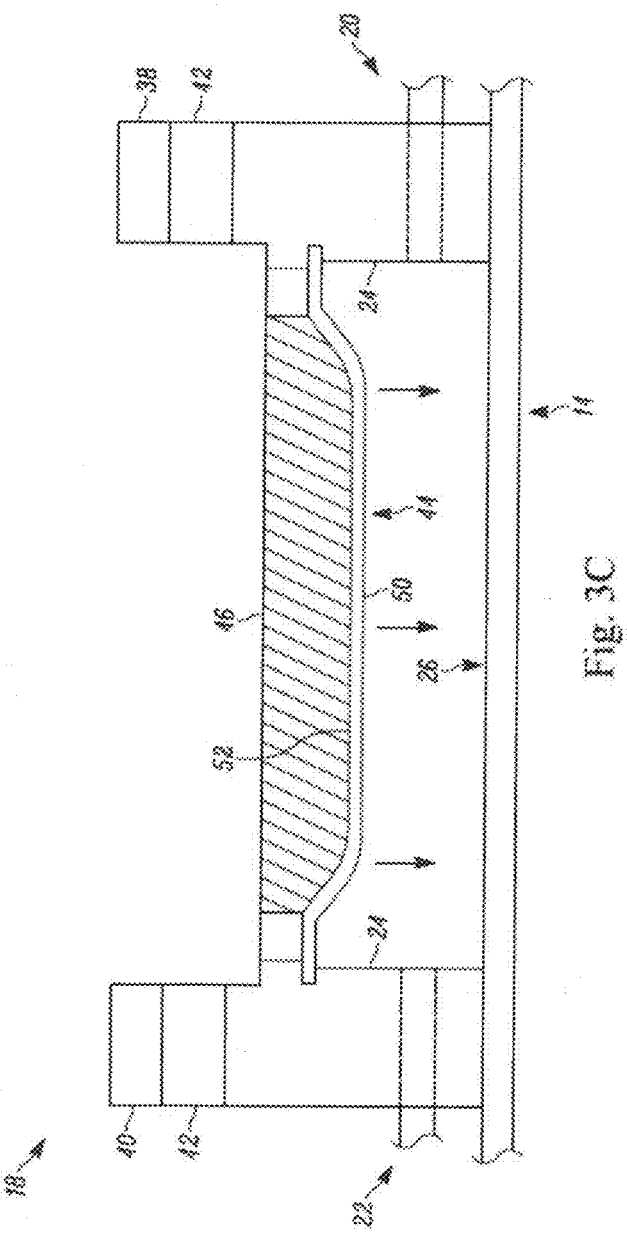

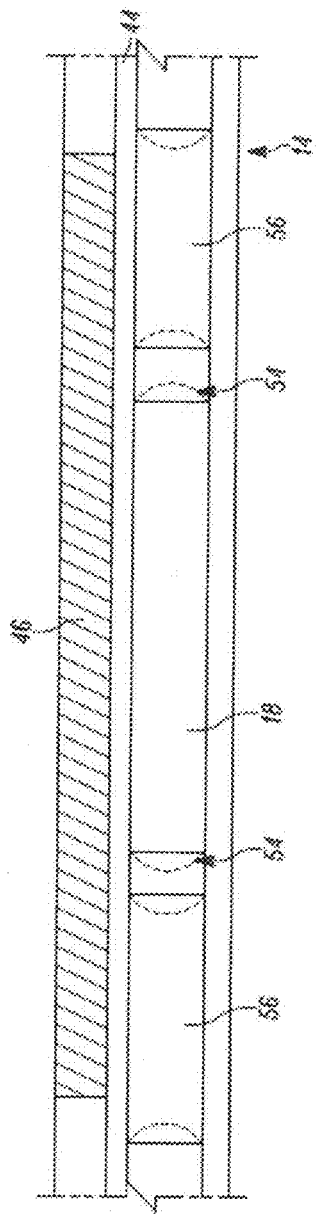

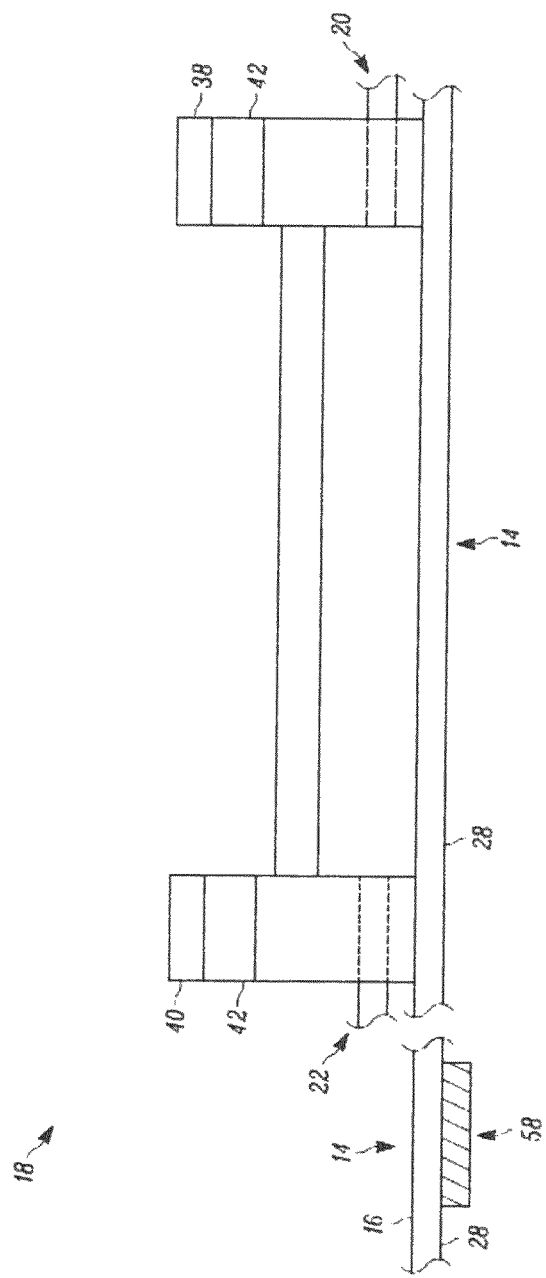

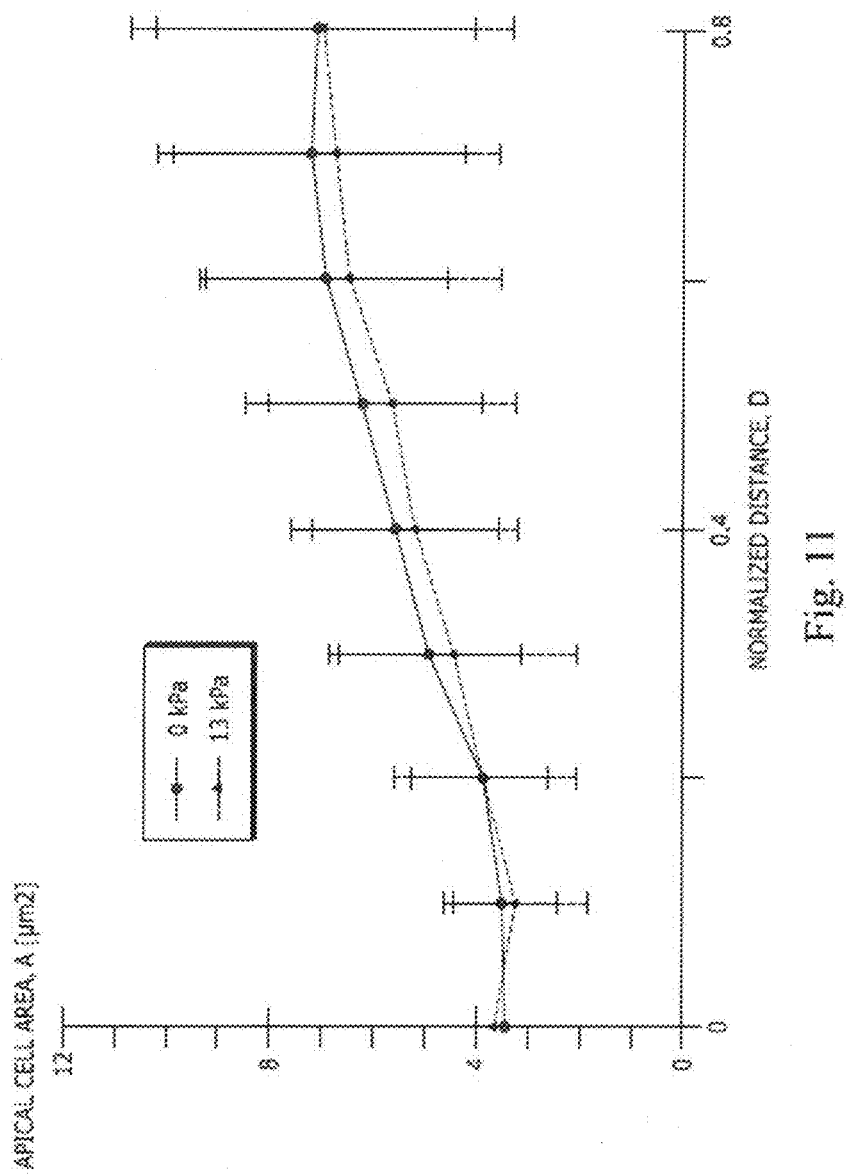

MICROFLUIDIC DEVICES, SYSTEMS, AND METHODS FOR EVALUATING TISSUE SAMPLES

RELATED APPLICATIONS

This application claims the benefit of U.S. Provisional Patent Application Ser. No. 62/011,146, filed Jun. 12, 2014, and 62/138,043, filed Mar. 25, 2015, the entirety of each of which is hereby incorporated by reference for all purposes.

TECHNICAL FIELD

The present disclosure relates generally to microfluidic devices and, more particularly, to microfluidic devices, systems, and methods for evaluating tissue samples as a function of a multitude of stimuli.

BACKGROUND

Microfluidic devices have significantly enhanced the speed, accuracy, and depth of research and development over the course of the past two decades. These devices are typically used to perform sophisticated chemical and biological analyses. One distinct advantage that such lab-on-a-chip technology has provided is the ability to work with very small samples, including molecules and cells.

A microfluidic device has a network of chambers connected by channels; although, some devices simply comprise channels. The channels have microscale dimensions and small quantities of specific liquids can be flowed through these channels. Microfluidic devices may be made at relatively low cost and the channels can be fabricated to perform different types of analytical processes, such as electrophoresis and pressure gradient flow by applying voltage, current, or electrical power to the flow liquid. For example, DNA may be analyzed through the use of a microfluidic device; the microfluidic channels in the specified device may be made compatible with electrophoresis techniques.

The capabilities of existing diagnostic techniques have been improved using microfluidic devices and methods. While these improvements have addressed specific biological issues such as keeping cells alive ex vivo, these existing systems generally relate to analyzing cellular or molecular compounds instead of larger samples. Additionally, these existing systems fail to provide a systems-level understanding of organ development and homeostasis as such systems cannot identify and integrate the multiple intrinsic and extrinsic factors that influence tissue size.

SUMMARY

The present disclosure relates generally to microfluidic devices and, more particularly, to microfluidic devices, systems, and methods for evaluating tissue samples as a function of a multitude of stimuli.

One aspect of the present disclosure relates to a microfluidic device for evaluating a tissue sample. The microfluidic device can include a tissue chamber, a liquid inlet channel, a liquid outlet channel, and at least one of components (1)-(3). The tissue chamber can be defined by a plurality of walls, at least one of the plurality of walls being transparent. The liquid inlet channel and the liquid outlet channel can be in fluid communication with the tissue chamber. Components (1)-(3) can include: (1) a deformable membrane disposed within the tissue chamber and being configured to oscillate, upon application of pressure thereto, to mechanically compress the tissue sample; (2) first and second electrodes disposed about the tissue chamber and being configured such that delivery of electrical energy thereto creates an electrical gradient across the tissue chamber; and (3) at least one deformable wall, which partially defines the tissue chamber and is configured to stretch either uniaxially or biaxially upon application of negative pressure to the tissue chamber.

Another aspect of the present disclosure relates to a system for evaluating a tissue sample. The system can include one or more microfluidic devices, a liquid source, a central acquisition and control module, and an imaging modality. Each of the microfluidic devices can include a tissue chamber, a liquid inlet channel, a liquid outlet channel, and at least one of components (1)-(3). The tissue chamber can be defined by a plurality of walls, at least one of the plurality of walls being transparent. The liquid inlet channel and the liquid outlet channel can be in fluid communication with the tissue chamber. Components (1)-(3) can include: (1) a deformable membrane disposed within the tissue chamber and being configured to oscillate, upon application of pressure thereto, to mechanically compress the tissue sample; (2) first and second electrodes disposed about the tissue chamber and being configured such that delivery of electrical energy thereto creates an electrical gradient across the tissue chamber; and (3) at least one deformable wall, which partially defines the tissue chamber and is configured to stretch either uniaxially or biaxially upon application of negative pressure to the tissue chamber. The liquid source can be in fluid communication with the liquid inlet channel. The central acquisition and control module can be in electrical communication with the liquid source and the translational microscopy stage. The imaging modality can be in electrical communication with the central acquisition and control module.

Another aspect of the present disclosure relates to a method for evaluating a tissue sample. One step of the method can include providing a system. The system can include one or more microfluidic devices, a liquid source, a central acquisition and control module, and an imaging modality. Each of the microfluidic devices can include a tissue chamber, a liquid inlet channel, a liquid outlet channel, and at least one of components (1)-(3). The tissue chamber can be defined by a plurality of walls, at least one of the plurality of walls being transparent. The liquid inlet channel and the liquid outlet channel can be in fluid communication with the tissue chamber. Components (1)-(3) can include: (1) a deformable membrane disposed within the tissue chamber and being configured to oscillate, upon application of pressure thereto, to mechanically compress the tissue sample; (2) first and second electrodes disposed about the tissue chamber and being configured such that delivery of electrical energy thereto creates an electrical gradient across the tissue chamber; and (3) at least one deformable wall, which partially defines the tissue chamber and is configured to stretch either uniaxially or biaxially upon application of negative pressure to the tissue chamber. The liquid source can be in fluid communication with the liquid inlet channel. The central acquisition and control module can be in electrical communication with the liquid source and the translational microscopy stage. The imaging modality can be in electrical communication with the central acquisition and control module. Next, a tissue sample can be placed in the tissue chamber. The system can then be operated to apply at least one extrinsic stimulus to the tissue sample, whereafter data generated as a result of the applied at least one extrinsic stimulus can be obtained. The obtained data can then be evaluated.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 1B is a cross-sectional view taken along Line 1B-1B in FIG. 1A;

FIG. 3B is a cross-sectional view taken along Line 3B-3B in FIG. 3A;

FIG. 3C shows the application of pressure to a deformable membrane comprising the tissue chamber in FIG. 3B;

FIG. 4B is a cross-sectional view taken along Line 4B-4B in FIG. 4A;

FIG. 5 is a cross-sectional view showing a piezoelectric element associated with a microfluidic device of the present disclosure;

In FIG. 8A, the chamber was flooded with 0.2% BSA in PBS to prevent sticking, followed by perfusion of WM1 media until fluid continuity is achieved (no air bubbles). In FIG. 8B, the imaginal disc was pipetted over the fluid outlet and positioned doral-side-first in a small bubble of WM1. In FIG. 8C, the imaginal disc was gently pulled into the chamber by sucking media through from the fluid outlet. In FIG. 8D, the imaginal disc was moved for confocal imaging and tubing was connected for perfusion, pressure, etc.;

FIG. 11 is a graph showing the results of Example 2.

DETAILED DESCRIPTION

Definitions

Figure 1A:
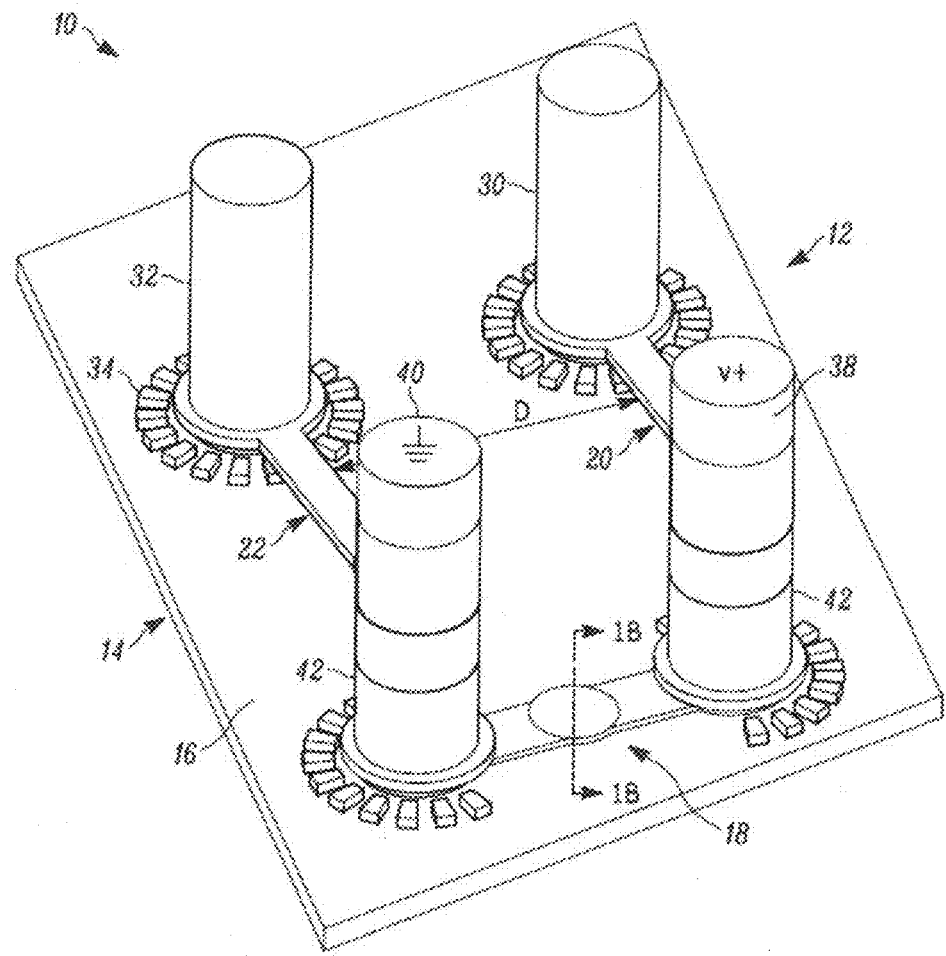
FIG. 1A is perspective view of a microfluidic device for evaluating a tissue sample constructed in accordance with one aspect of the present disclosure.

Unless defined otherwise, all technical and scientific terms used herein have the same meaning as is commonly understood by one of skill in the art to which the present disclosure pertains.

In the context of the present disclosure, the term "subject" can be used interchangeably with the term "patient" and refer to any organism including, but not limited to, human beings, pigs, rats, mice, dogs, goats, sheep, horses, monkeys, apes, farm animals, livestock, rabbits, cattle, insects (e.g., *Drosophila*), fish (e.g., zebrafish), etc.

As used herein, the term "tissue sample" can refer intact, unprocessed biological tissues. A tissue sample can include an aggregate of cells, whether they are a part of a tissue explant or a part of an organ, an organoid, or a model organism, such as a *Drosophila* wing imaginal disc, or cellular aggregates or organoids from embryonic or induced pluripotent stem cells that are undifferentiated, partially differentiated, or terminally differentiated. The cells in a particular tissue sample can include the same or several different cell types. In some instances, a tissue sample can be obtained or derived from any portion of a subject, with or without biological processing using cell and stem cell engineering methods. In other instances, one or more cells comprising a tissue sample can be genetically modified, either prior to or during analysis by the present disclosure, to express one or more detectable labels (e.g., GFP).

As used herein, the term "in electrical communication" can refer to a first item or component that is directly or indirectly coupled to a second item or component by at least one conducting medium (e.g., a wire).

As used herein, the term "labeling agent" can refer to any compound, moiety, or agent capable of being detected by an imaging modality. A labeling agent can be chromogenic, fluorescent or chemiluminescent. Non-limiting examples of labeling agents can include fluorophore-conjugated antibodies, fluorescent small molecule dyes, fluorescent in situ-hybridized antisense RNA (see, for example, Cheung L S et al., *Methods Mol Biol.* 2015; 1189:115-22), fluorogenic azide probes (see, for example, Shieh, P. et al., *J Am Chem Society* 137(22):7145-7151 (2015), and labeled metabolites bound to tissue through the fixation process. Other examples of labeling agents can include fluorescent-tagged chemical or biological species (e.g., proteins, mRNA, etc.) that are transfected or expressed stably by cells comprising the tissue sample (see, for example, Huang, J. et al., *PNAS*, 106(20): 8284-8289 (2009); Chen, T-W et al., *Nature*, 499(7458): 295-300 (2013); and Elliot, D A et al., *Methods Mol Biol.*, 420:79-95 (2008)).

As used herein, the term "in fluid communication" can refer to a communication between two sections, components, or features of the microfluidic devices and systems of the present disclosure. In some instances, this communication may be a direct connection or a direct path between two sections, components, or features or, alternatively, may include one or more intervening sections in the path between two sections, components, or features of the microfluidic devices and systems of the present disclosure.

As used herein, the term "port" can refer to an opening, recess, or a cavity for providing a pathway for the passage of a liquid or a fluid.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

The present disclosure relates generally to microfluidic devices and, more particularly, to microfluidic devices, systems, and methods for evaluating tissue samples as a function of a multitude of stimuli. To develop an integrated understanding of the complicated process of cellular differentiation, cell and tissue size control and growth termination, three essential experimental requirements need to be met: (1) the local environment needs to be precisely controlled; (2) the model organ system needs to be well described genetically so that cell processes can be intrinsically manipulated; and (3) the system needs to have a favorable size and geometry for imaging with cellular resolution.

Advantageously, the present disclosure provides microfluidic devices, systems, and methods that merge two ideas—cell culture in microfluidic devices for long-term control of culture conditions with devices for analysis of larger hierarchical structures of entire organisms—to form a controlled microenvironment with live-imaging capabilities in a genetically-modifiable system that enables a systematic investigation into the response of tissue samples to genetic, chemical, mechanical, and electrical perturbations. Application of multiple stimuli by the microfluidic devices, systems, and methods of the present disclosure is computer-controlled, which advantageously permits coordination of multiple stimuli and readouts according to preprogrammed experimental protocols. Thus, as discussed below, stimuli can be modulated during a given experiment through on-line processing of tissue imaging data, which provides control-loop feedback and permits directed process control of tissue samples for application to cellular or tissue differentiation and growth regulation. Consequently, the sequence of stimuli perturbations and the imaging sequence(s) can be scheduled and thereby lead to lower phototoxicity.

Further applications and advantages of the present disclosure are discussed below.

Microfluidic Devices

One aspect of the present disclosure can include a microfluidic device 10 (FIGS. 1A-B) for evaluating a tissue sample to study, for example, the effect(s) of exogenous stimuli on growth and development of the tissue sample. The microfluidic device 10 can have a two-layer configuration comprising a feature side 12 that is coupled to a transparent (or substantially transparent) substrate 14. As described in detail below, the feature side 12 can include various structural components and features of the microfluidic device 10. All or only a portion of the structural components and features can be formed from one or combination of materials, such as a polymeric organosilicon compound (e.g., polymethylsiloxane or PDMS), polystyrene, glass, quartz, and the like. The substrate 14 can be optically clear and capable of transmitting light therethrough. In one example, the substrate 14 can be formed from glass (e.g., a coverslip). The structural components and features that form the feature side 12 of the microfluidic device 10 can be coupled to a first major surface 16 of the substrate 14 using one or a combination of attachment techniques, such as suction, chemical bonding (e.g., adhesives or plasma treatment), clamps, and the like.

Various manufacturing methods can be used to form the microfluidic device 10, as will be appreciated by those in the art. Exemplary methods include, but are not limited to, a variety of micromachining and microfabrication techniques, including film deposition processes such as spin coating, chemical vapor deposition, laser fabrication, photolithographic and other etching techniques using either wet chemical processes or plasma processes, embossing, injection molding and bonding techniques. In addition, there are printing techniques for the creation of desired fluid guiding pathways; that is, patterns of printed material can permit directional fluid transport. In one example, soft lithography can be used to form all or only a portion of a microfluidic device 10.

In one example, a microfluidic device 10 can comprise a tissue chamber 18, a liquid inlet channel 20 in fluid communication with the tissue chamber, a liquid outlet channel 22 in fluid communication with the tissue chamber, and at least one of the following components, which are described in more detail below: (1) a deformable membrane disposed within the tissue chamber and being configured to oscillate, upon application of pressure thereto, to mechanically compress the tissue sample; (2) first and second electrodes disposed about the tissue chamber and being configured such that delivery of electrical energy thereto creates an electrical gradient across the tissue chamber; and (3) at least one deformable wall, which partially defines the tissue chamber and is configured to stretch either uniaxially or biaxially upon application of negative pressure to the tissue chamber.

The tissue chamber 18 can be defined by a plurality of walls 24, at least one of which is transparent. As shown in FIG. 1B, the transparent wall 26 defining a portion of the tissue chamber 18 can comprise a portion of the substrate 14 (e.g., a portion of the first major surface 16). The remainder of the tissue chamber 18 can be defined by the walls 24 associated with the feature side 12 of the microfluidic device 10. In some instances, one or more interior surfaces defining the tissue chamber 18 can include a groove (not shown) or grooves to permit liquid flow around the tissue sample. Although the tissue chamber 18 is depicted as having a disc-shaped configuration in FIG. 1A, it will be appreciated that other shapes are possible (e.g., square, rectangular, cylindrical). In one example, the tissue chamber 18 can have a disc-shaped configuration with a diameter of between about 1-4 mm (e.g., 1.4 mm). In another example, the tissue chamber 18 can have a cylindrical and rotatable configuration to enable 360-degree viewing of the tissue sample.

As mentioned above, the substrate 14 can be transparent (or substantially transparent) (e.g., a glass coverslip). The substrate 14 can include oppositely disposed first and second major surfaces 16 and 28. In some instances, the portion of the substrate 14 that forms the tissue chamber 18 can include an embedded or etched marker (or markers) (not shown) to facilitate orientation of the microfluidic device 10. In one example, such a marker can include an embedded fluorescent scale bar or a QR code to facilitate repetitive measurements. In other instances, the substrate 14 can be instrumented. Electrode arrays (not shown), for example, can be patterned on the surface(s) 16 and 28 of the substrate 14 to give a spatial readout of local voltage, or to apply a voltage at specific spatial locations. Examples of methods for patterning electrode arrays on glass can include deposition and lithographic patterning of gold or indium tin oxide, as well as ink jet printing. In further instances, patterned electrode arrays or electrical channels can be used to measure a cascade of action potentials generated by certain cells within the tissue chamber 18 (e.g., upon application of mechanical compression thereto).

Referring to FIG. 1A, a liquid inlet channel 20 can extend between the tissue chamber 18 and a liquid inlet 30 or port. In some instances, an interior surface of the liquid inlet channel 20 can be textured to induce local turbulence in a liquid flowing therethrough to improve penetration of a labeling agent (or agents) into a tissue sample (see, e.g., Stott S L et al., *PNAS* 107:18392-18397, 2010). Although one liquid inlet channel 20 is shown in FIG. 1A, it will be appreciated that a greater number of liquid inlet channels can be included. Because of the limited mixing associated with multiple liquid inlet channels 20, for example, liquid flow in the microfluidic device 10 can be patterned since different regions of the tissue sample can receive multiple mixtures of different labeling cell/tissue culture media (see, for example, Frampton, J P et al., *Biotechnology Journal*, 10(1):121-125 (2015)). In one example, the length of the liquid inlet channel 20 can be between about 6-9 mm (e.g., 7.5 mm).

A liquid outlet channel 22 can extend between the tissue chamber 18 and a liquid outlet 32 or port. Although one liquid outlet channel 22 is shown, it will be appreciated that a greater number of liquid outlet channels can be included. In one example, the length of the liquid outlet channel 22 can be between about 6-9 mm (e.g., 7.5 mm). In some instances, the liquid inlet channel 20 and the liquid outlet channel 22 can be spaced apart from each other by a distance D of about 1-4 mm (e.g., 2 mm). In other instances, the length of the liquid inlet channel 20 can be the same as, or different than, the length of the liquid outlet channel 22.

The microfluidic device 10 can include any number and configuration of fiducial markers 34 to assist in orienting the device and facilitating repetitive measurements. As shown in FIG. 1A, a plurality of fiducial markers 34 can be placed in a circular pattern about the liquid outlet 32 and the liquid inlet 30. It will be appreciated that one or more fiducial markers 34, arranged in any desired pattern, can be placed about other components of the microfluidic device 10, such as the tissue chamber 18.

Figure 2:
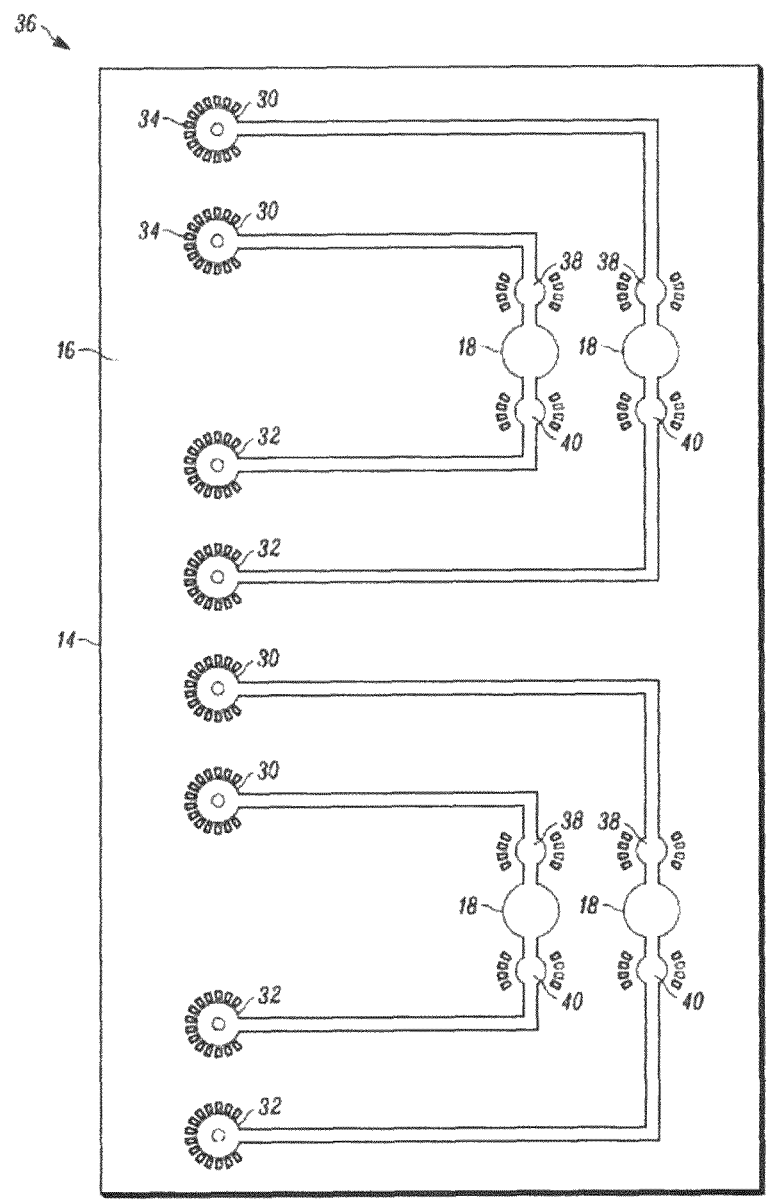
FIG. 2 is a plan view showing four microfluidic devices (FIG. 1A) arranged in a multiplex array.

The microfluidic device 10 can be constructed using a modular design to allow assembly into arrays for high-throughput applications. As shown in FIGS. 2 and 4C, for example, four microfluidic devices 10 can be formed as a single array 36 for multiplex analysis. In FIG. 2, the array 36 can include for separate tissue chambers 18, and their associated liquid inlet and outlet channels 20 and 22, all of which are disposed on a single transparent substrate 14 (e.g., a glass coverslip).

As mentioned above, the microfluidic device 10 can include at least one of components (1)-(3). FIGS. 1A-B illustrate one example of a microfluidic device 10 including first and second electrodes 38 and 40 that are disposed about the tissue chamber 18. Standard tissue culture wells do not permit the simulation of electrical gradients. Bioelectrical signals provide another layer of regulation of cell fate and growth; however, cross-regulation of chemical signaling pathways with electrical signals is poorly understood. As discussed below, the ability of the present disclosure to create an electrical gradient across a tissue chamber 18 permits single-cell analysis of physiological electrical gradients on development.

As such, the first and second electrodes 38 and 40 can be configured so that delivery of electrical energy thereto creates an electrical gradient across the tissue chamber 18. Advantageously, creation of the electrical gradient invokes a reaction by the tissue sample, which can be assessed and studied according to certain aspects of the present disclosure. The first and second electrodes 38 and 40 can be located atop respective plugs 42, which prevent escape of a liquid from the liquid inlet channels 20 and the liquid outlet channels 22 (respectively). In one example, a plug 42 can be made of agar. Therefore, in some instances, the first and second electrodes 38 and 40 are indirectly connected to the liquid inlet and liquid outlet channels 20 and 22. The first and second electrodes 38 and 40 can be spaced apart from one another, and from the tissue chamber 18, at a distance sufficient to create the electrical gradient. Although not shown, the first and second electrodes 38 and 40 can be in electrical communication with a power source for providing electrical energy thereto. As shown in FIG. 1A, the post-like structures comprising the first and second electrodes 38 and 40 can be at least partially surrounded by a plurality of fiducial markers 34.

Figure 3A:
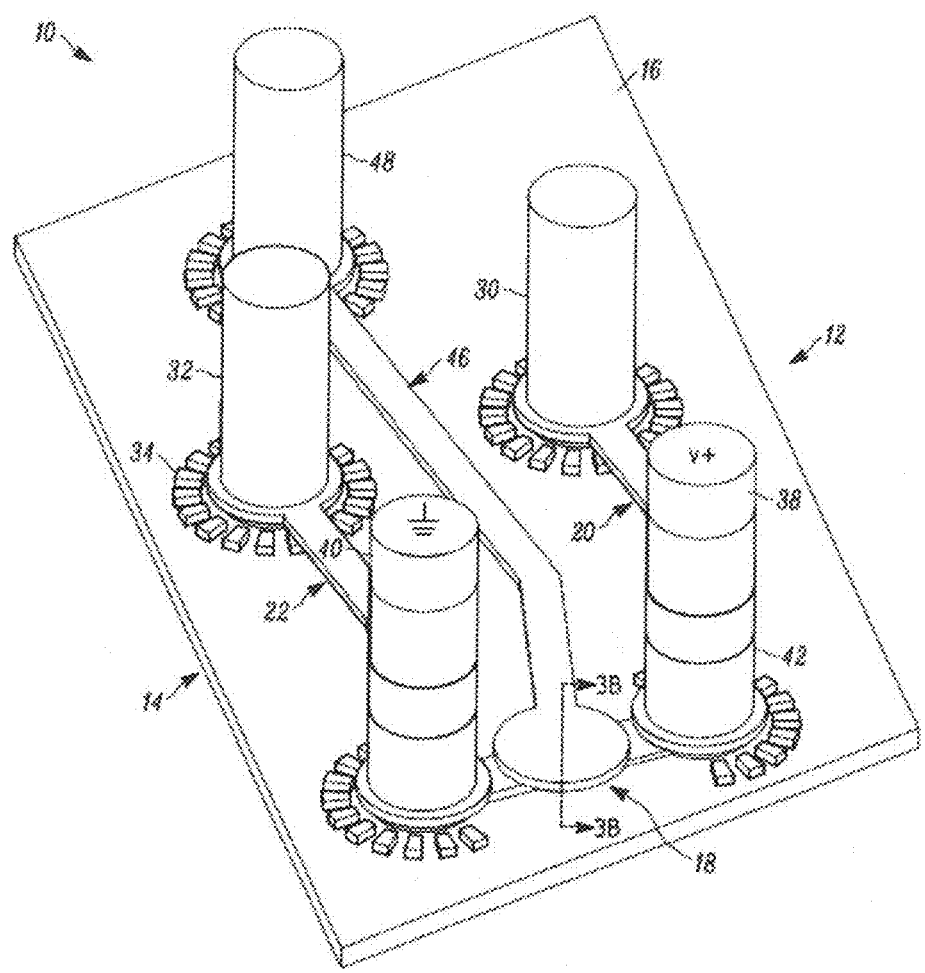
FIG. 3A is perspective view of a microfluidic device for evaluating a tissue sample constructed in accordance with another aspect of the present disclosure.

Another example of a microfluidic device 10 is illustrated in FIGS. 3A-B. In this example, the microfluidic device 10 can comprise a deformable membrane 44 (component (1)) as well as first and second electrodes 38 and 40 (component (2)). In addition to the deformable membrane 44, the microfluidic device 10 can include a pressure line 46 and a pressure port 48 adapted to receive positive or negative pressure. The deformable membrane 44 can be configured to selectively oscillate, upon application of pressure thereto (e.g., by means of an applied pressure signal), to mechanically compress the tissue sample (e.g., by increasing pressure within the tissue chamber and/or decreasing the height of the tissue chamber 18). The deformable membrane 44 can be comprised of a flexibly resilient material (e.g., PDMS). The deformable membrane 44 can be disposed within the tissue chamber 18 such that a lower surface 50 of the membrane forms an upper surface that defines the interior of the tissue chamber. The pressure line 46 can be in fluid communication with an upper surface 52 of the membrane 44 to enable application of pressure to the upper surface. For example, the pressure line 46 can be located above the portion of the tissue chamber 18 comprising the membrane 44.

Figure 4A:
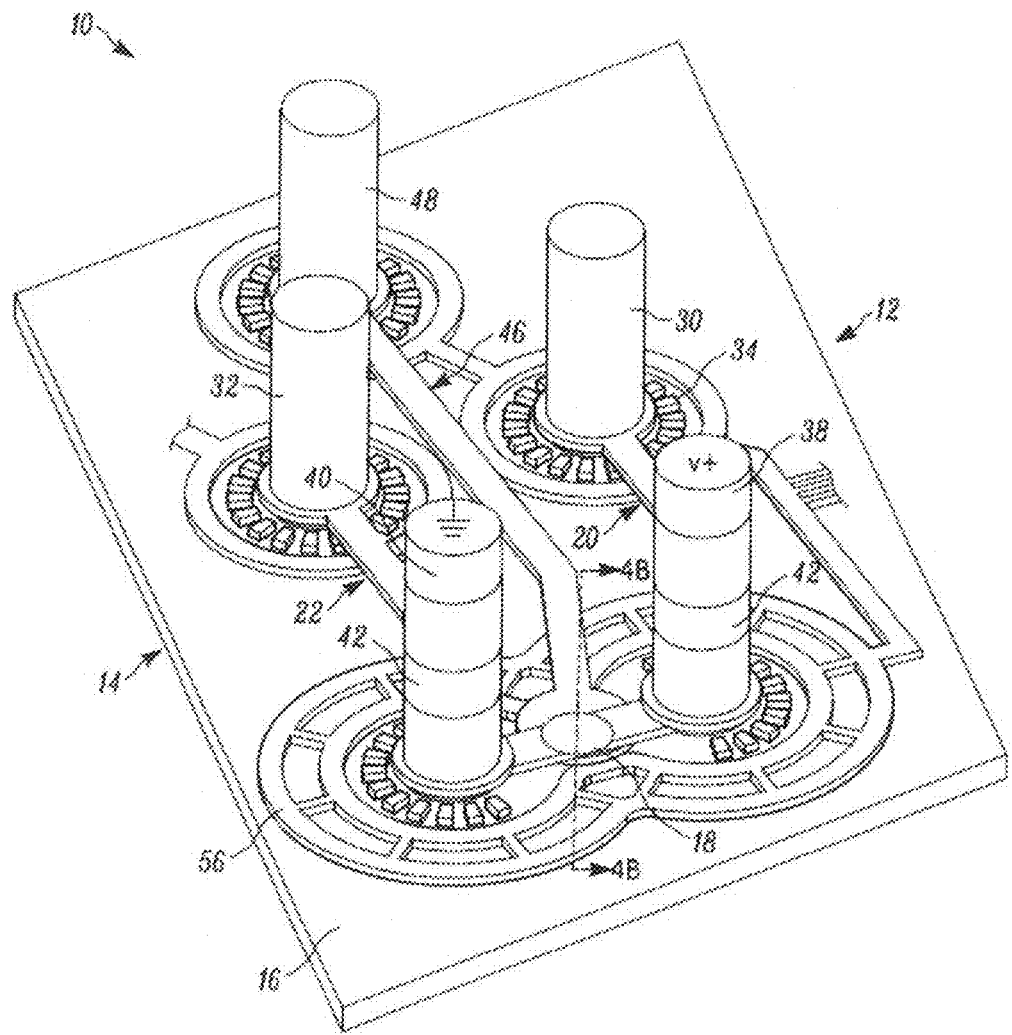
FIG. 4A is perspective view of a microfluidic device for evaluating a tissue sample constructed in accordance with another aspect of the present disclosure.
Figure 4C:
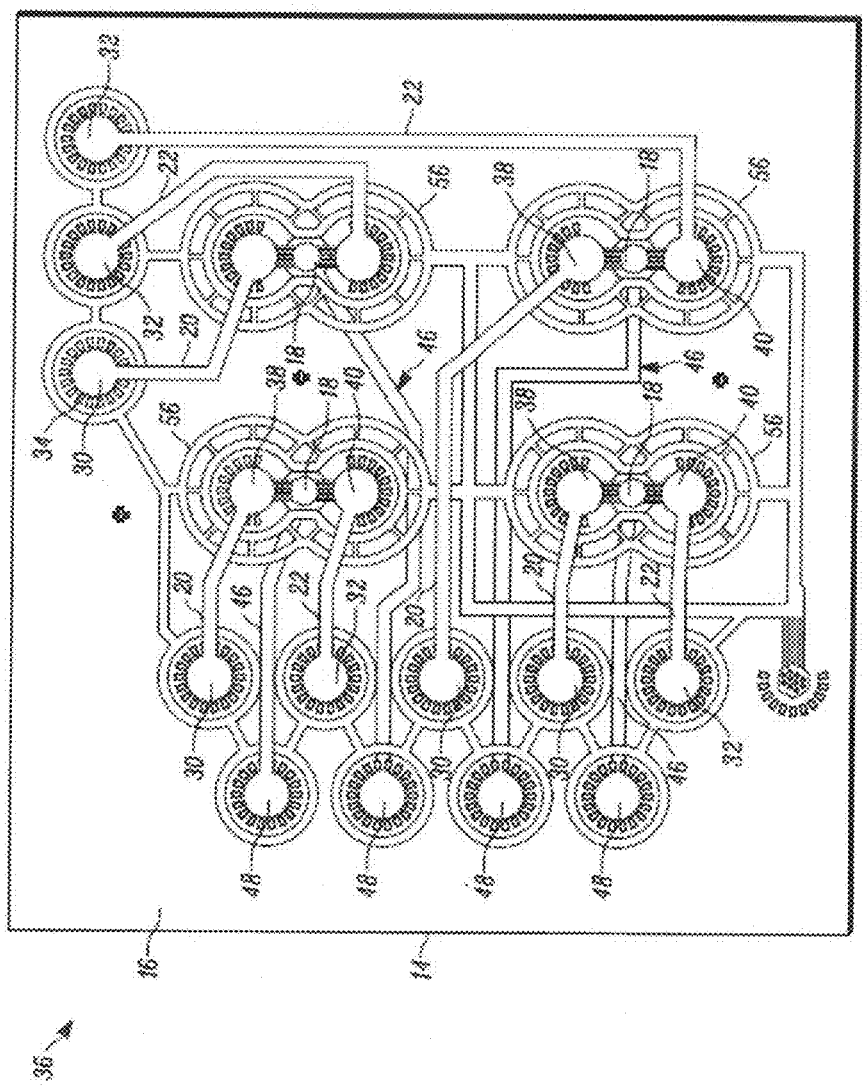
FIG. 4C is a plan view showing four microfluidic devices (FIG. 4A) arranged in a multiplex array.

Another example of a microfluidic device 10 is illustrated in FIGS. 4A-C. In this example, the microfluidic device 10 can comprise a deformable membrane 44 (component (1)), first and second electrodes 38 and 40 (component (2)), and at least one deformable wall 54 (component (3)). The deformable wall 54 can at least partially define the tissue chamber 18 and be configured to stretch upon application of pressure thereto. Pressure (e.g., negative pressure) can be applied to the deformable wall 54 by one or more vacuum lines 56 that abut or are adjacent to the deformable wall. In some instances, a hydro-mold material (e.g., a porous calcium alginate precursor that is cross-linked in situ) (not shown) can be disposed in the tissue chamber 18 so that it partially or completely encapsulates the tissue sample. In such instances, the modulus of the hydro-mold can be tuned to match the modulus of the tissue sample (e.g., by varying the cross-linker density). In one example, where a vacuum line 56 abuts only one deformable wall 54, the application of negative pressure to the deformable wall can cause uniaxial stretching of the wall. In another example, where a vacuum line 56 abuts opposing deformable walls 54, the application of negative pressure to each of the deformable walls can cause biaxial stretching thereof (FIG. 4B). Advantageously, as the wall(s) 54 deform, a tensile stress can be transmitted through the hydromold network, which, in turn applies a tensile stress to the tissue sample.

In another example, the microfluidic device 10 can additionally or optionally include one or more piezoelectric elements 58 (FIG. 5) that, upon delivery of an oscillatory voltage thereto, induces a vibration that propagates through the substrate 14 and the tissue chamber 18 into the tissue sample. Advantageously, this facilitates penetration (e.g., by increasing effective diffusion) of a labeling agent (or agents) into a tissue sample located in the tissue chamber 18. One example of a piezoelectric element 54 is described by Yazdi, S. et al., *Biomicrofluidics* 6, 044114 ((2012). In some instances, a piezoelectric element 58 can be connected to the second major surface 28 of the substrate 14 by glue. In other instances, a piezoelectric element 58 can be connected to the second major surface 28 of the substrate 14 by a non-adhesive gel so that the piezoelectric element is reusable. The piezoelectric element 58 can be located about the substrate 14 so that it does not interfere with imaging of the tissue sample. For example, the piezoelectric element 58 is not connected to the portion of the substrate 14 that is directly adjacent the tissue chamber 18 where the passage of light is required to obtain image data.

In another example, the microfluidic device 10 can additionally or optionally include one or more microwaves (not shown) coupled or connected thereto. One example of a microwave that can be connected to the microfluidic device 10 is described by Issadore, D. et al., *Lab. Chip* 9, 1701 (2009). Such a microwave can be operated to drive a labeling agent (e.g., polar antibodies) deep into the tissue sample during operation of the microfluidic device 10.

It will be appreciated that any of the components and features discussed above can be combined or omitted to form a microfluidic device 10, or array 36, of the present disclosure. One skilled in the art can determine such combinations based, for example, upon the particular application of the microfluidic device 10 or array 36. For example, one skilled in the art will appreciate that a microfluidic device 10 comprising only component (1), only component (3), components (2) and (3), or components (1) and (3) are also possible.

Systems

Another aspect of the present disclosure can include a system 60 (FIG. 6) for evaluating a tissue sample as a function of a multitude of stimuli. The system 60 can comprise one or more microfluidic devices 10, a liquid source 62, a central acquisition and control module 64, and an imaging modality 66. Each of the microfluidic devices 10 can include a tissue chamber 18, a liquid inlet channel 20, a liquid outlet channel 22, and at least one of components (1)-(3). The tissue chamber 18 can be defined by a plurality of walls 24, at least one of the plurality of walls being transparent. The liquid inlet channel 20 and the liquid outlet channel 22 can be in fluid communication with the tissue chamber 18. Components (1)-(3) can include: (1) a deformable membrane 44 disposed within the tissue chamber 18 and being configured to oscillate, upon application of pressure thereto, to mechanically compress the tissue sample; (2) first and second electrodes 38 and 40 disposed about the tissue chamber and being configured such that delivery of electrical energy thereto creates an electrical gradient across the tissue chamber; and (3) at least one deformable wall 54, which partially defines the tissue chamber and is configured to stretch either uniaxially or biaxially upon application of negative pressure to the tissue chamber. The liquid source 62 can be in fluid communication with the liquid inlet channel 20. The central acquisition and control module 64 can be in electrical communication with the liquid source 62 and a translational microscopy stage 68. The imaging modality 66 can be in electrical communication with the central acquisition and control module 64.

In some instances, one or more of the microfluidic devices 10 comprising the system 60 can be constructed like the microfluidic device or array shown in FIGS. 4A-B and 4C, respectively. It will be appreciated, however, that the microfluidic device(s) 10 comprising the system 60 can have any of the other configurations described herein, as well as other combinations of components and features discussed herein but not specifically shown.

In some instances, the system 60 can include one or more liquid sources 62. The liquid source 62 can include any reservoir capable of holding a liquid (e.g., a cell/tissue culture media). In one example, the cell/tissue culture media can contain small molecule drugs, protein growth factors, defined or undefined media supplements, or be chemically-defined. An example of a chemically-defined medium for introduction of small molecules to affect cell processes is described by Burnette, M. et al., *Molecular BioSystems*, 10(10):2713-2723 (2014). Where the system 60 contains multiple liquid sources 62, the liquid contained in each of the liquid sources can be the same as or different than the liquid in the other liquid sources. In another example, the liquid source 62 can comprise a syringe pump or other type of pump, such as a peristaltic pump or a reciprocating pump.

One or more of the liquid sources 62 can be in fluid communication with a pump (not shown), which may additionally or optionally be in electrical communication with the central acquisition and control module 64. In such instances, the pump may also be connected to, and in fluid communication with, the liquid inlet 30 of the microfluidic device(s) 10.

Advantageously, the arrangement of the liquid source 62, pump(s), and liquid inlet and outlet channels 20 and 22 with the central acquisition and control module 64 enables computer-controlled liquid flow, which provides precise modulation of liquid perfusion (e.g., to evaluate the temporal dependence of extracellular biochemical signals on cellular responses). When interfaced with precise fluid delivery equipment (e.g., syringe pumps), a steady stream of fluid can gently transit the system 60, which, in turn, can provide a steady stream of liquids (e.g., cell/tissue culture media) to a developing tissue sample (e.g., an organ).

In some instances, the system 60 can include a vacuum source 70 (e.g., a pump). The vacuum source 70 can be in fluid communication with the vacuum line(s) 56 of the microfluidic device via tubing 72. In some instances, at least one valve 74 (e.g., an electro-pneumatic or manual valve) can be in fluid communication with the tubing 72. The valve 74 can also be in electrical communication with the central acquisition and control module 64 so that operation of the valve, and thus the amount of negative pressure applied to the microfluidic device 10, can be automatically controlled.

In some instances, the system 60 can include a pressure source 76 (e.g., a compressed air tank or canister). The pressure source 76 can be in fluid communication with one or more pressure lines 46 of the microfluidic device 10 via tubing 72. In some instances, a first valve 78 (e.g., an electro-pneumatic valve) and a second valve 80 (e.g., a manual valve) can be in fluid communication with the tubing 72. The first valve 78 can also be in electrical communication with the central acquisition and control module 64 so that operation of the first valve can be automatically controlled to modulate the amount of pressure applied to the microfluidic device 10.

In some instances, the central acquisition and control module 64 can include at least one computer and associated computational software programmed to operate components of the system 60. Non-limiting examples of computational software that can be included as part of the central acquisition and control module 64 can include software available from Imaris (BITPLANE AG, Zurich, Switzerland), LabVIEW (National Instruments, Austin, Tex.) and MetaMorph (Molecular Devices, Sunnyvale, Calif.). In some instances, the computer comprising the central acquisition and control module 64 can be interfaced with analog and digital output hardware (e.g., available from National Instruments) as well as hardware associated with the imaging modality 66. The central acquisition and control module 64 can be in electrical communication with all or only a portion of the components comprising the system 60. In some instances, the central acquisition and control module 64 can be in wired or wireless communication with all or only a portion of the components comprising the system 60. Advantageously, the central acquisition and control module 64 can be configured to automatically coordinate multiple stimuli and readouts with a preprogrammed experimental protocol. As the entire system 60 is computer-controlled, the sequence of stimuli perturbations and the imaging sequence can be scheduled. In this manner, imaging can be scheduled to capture relatively fast events (e.g., a calcium wave response to laser ablation) at high frame rates and slow events (e.g., mitosis) at a low frame rate. Advantageously, this imaging scheme only images the tissue sample when absolutely necessary, which can lead to lower phototoxicity. Additionally, the system 60 provides feedback control, which enables real-time control to change a stimulus (or stimuli) profile(s) as a result of a measured response of the biological tissue.

In some instances, the imaging modality 66 can include a confocal microscope, non-limiting examples of which include a spinning disc confocal microscope, a two photon confocal microscope, and a light-sheet based microscope. In other instances, the imaging modality 66 can include any microscope that includes selective plane illumination microscopy (SPIM) technology and/or is configured to perform SPIM. In this instance, the tissue chamber 18 can have a cylindrical and rotatable configuration to enable 360-degree viewing of the tissue sample.

Methods

Figure 7:
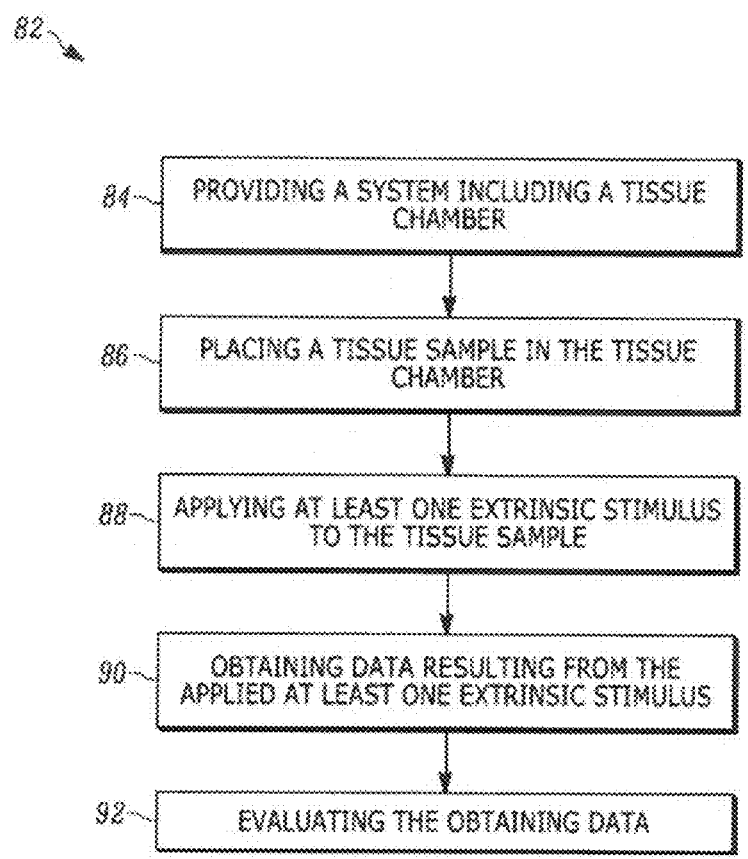
FIG. 7 is a process flow diagram illustrating a method for evaluating a tissue sample according to another aspect of the present disclosure.
Figure 8A:
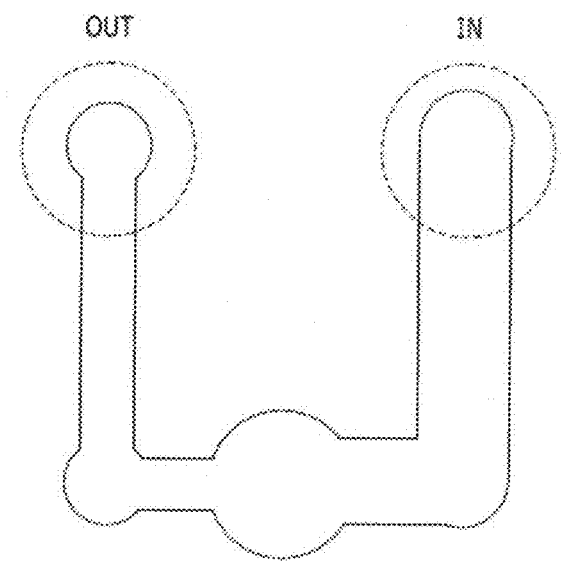
FIGS. 8A-D are schematic illustrations showing flow-loading of $3^{rd}$ instar *Drosophila* wing imaginal disc.
Figure 8B:
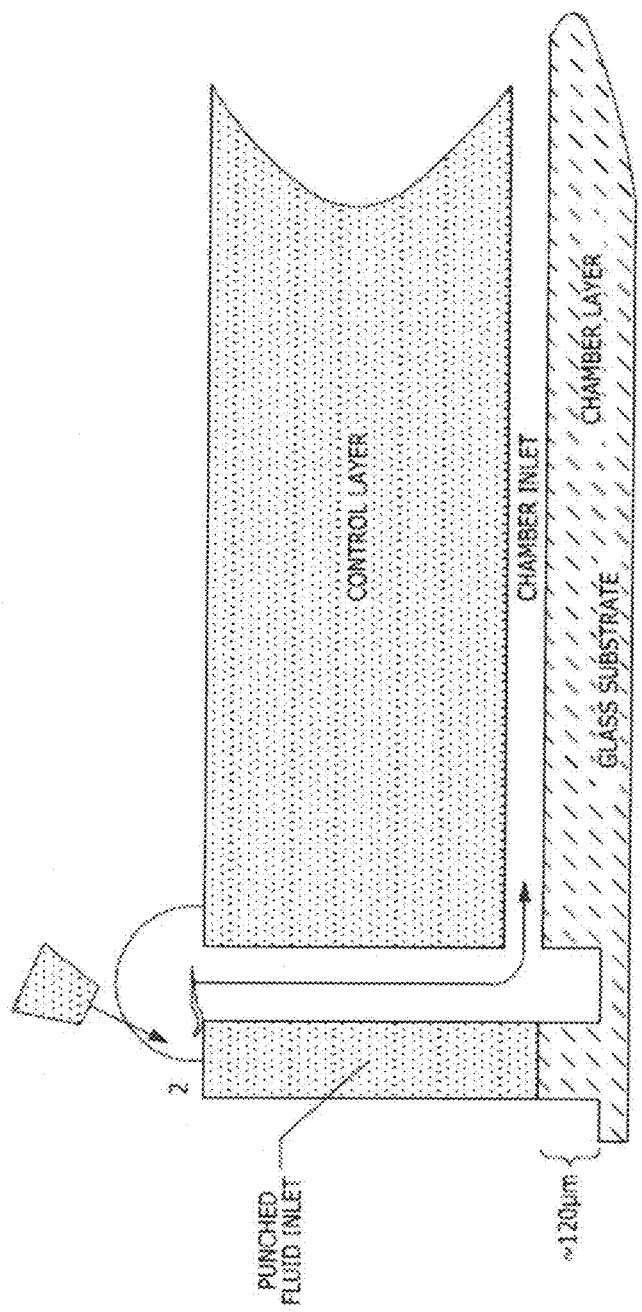
Figure 8C:
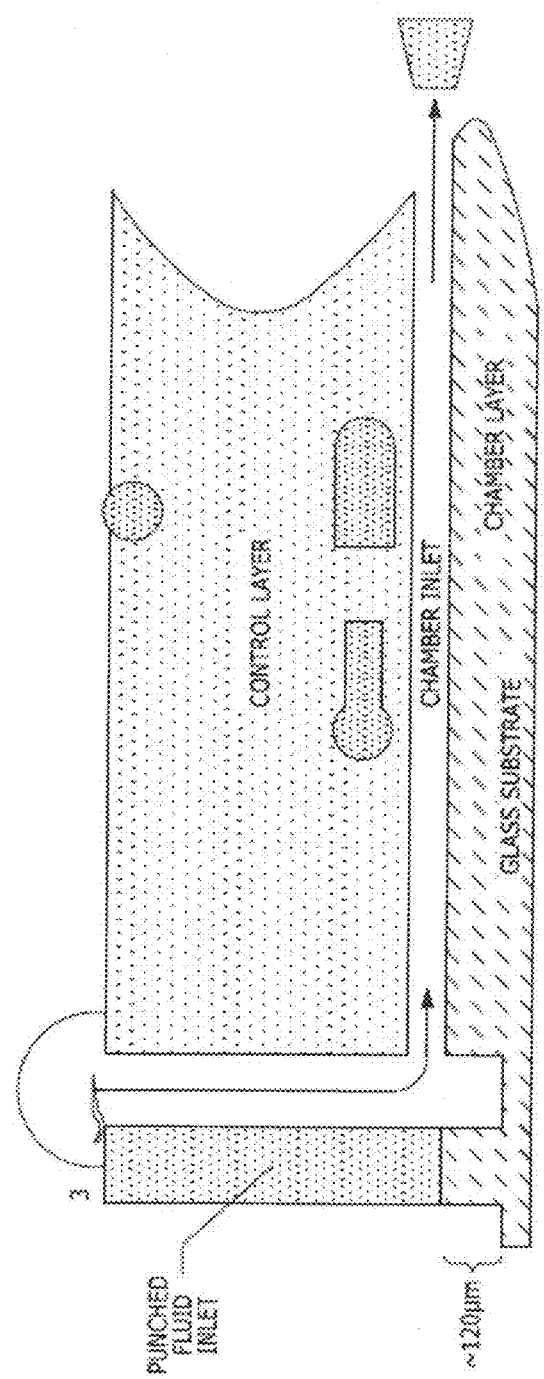
Figure 8D:
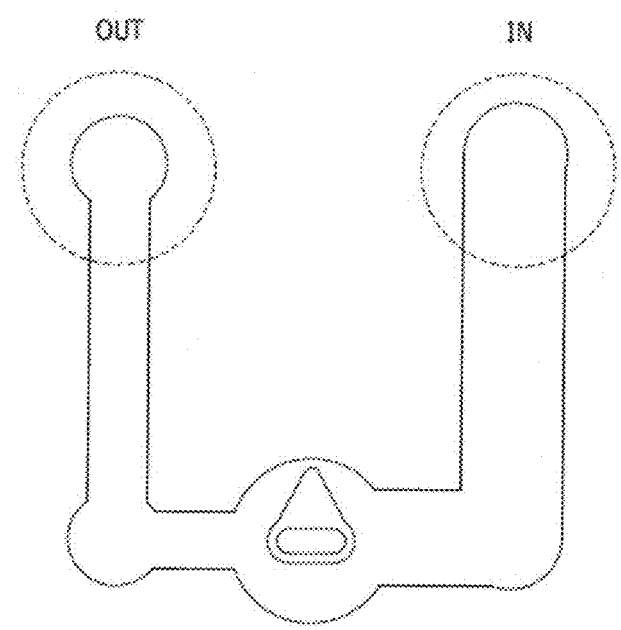

Another aspect of the present disclosure can include a method 82 (FIG. 7) for evaluating a tissue sample. The method 82 can generally include the steps of: providing a system 60 including one or more microfluidic devices 10 at least having a tissue chamber 18 and one or more of components (1)-(3), a liquid source 62, a central acquisition and control module 64, and an imaging modality 66 (Step 84); placing a tissue sample in the tissue chamber (Step 86); operating the system to apply at least one extrinsic stimulus to the tissue sample (Step 88); obtaining data generated as a result of the applied at least one extrinsic stimulus (Step 90); and evaluating the obtained data (Step 92).

Figure 6:
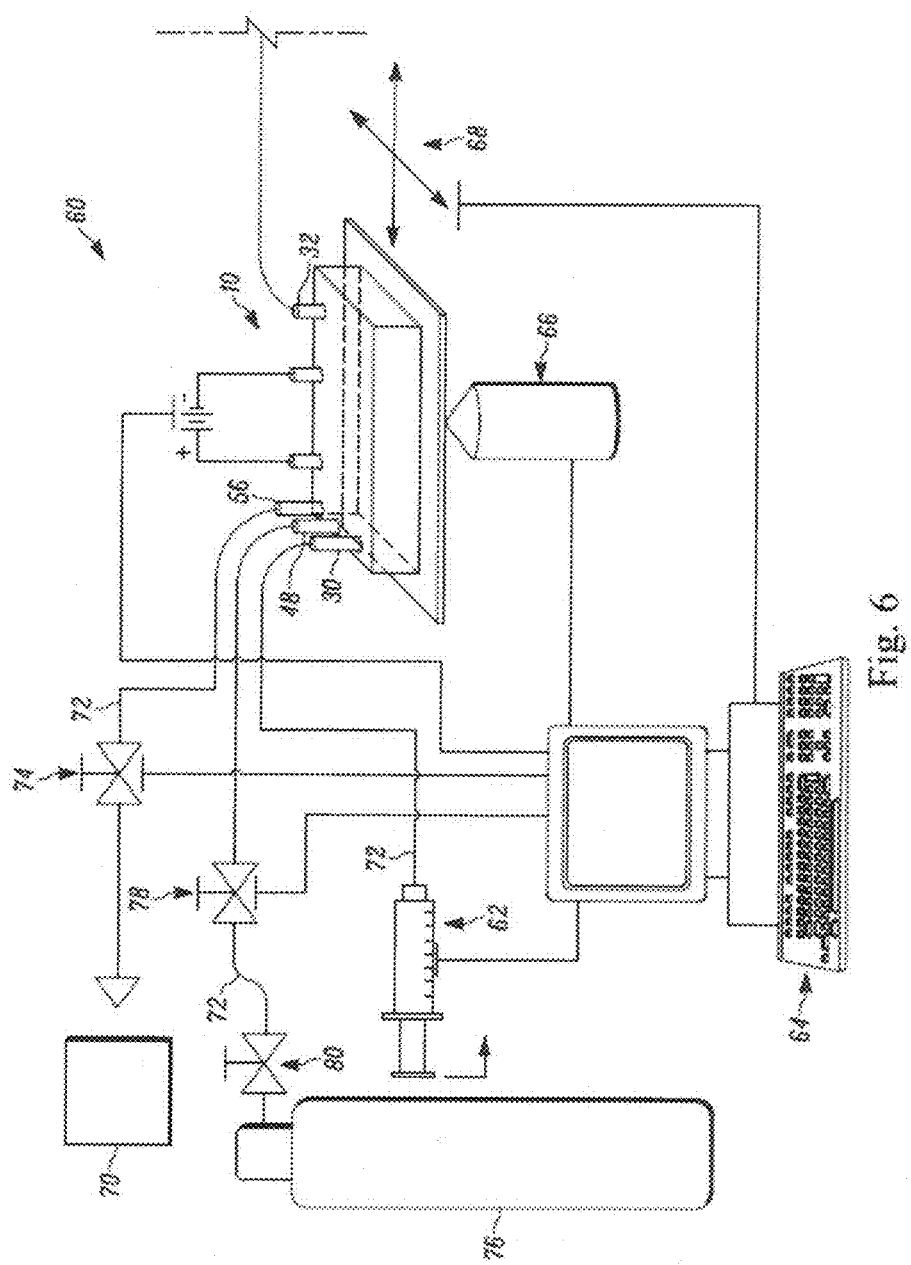
FIG. 6 is a schematic illustration of a system for evaluating a tissue sample according to another aspect of the present disclosure.

The system 60 provided at Step 84 can be identically or similarly constructed as the system shown in FIG. 6. One skilled in the art will appreciate that the configuration of the system 60 used in the method 82 can depend, for example, upon the particular application.

At Step 86, a tissue sample can be placed in the tissue chamber 18. Examples of tissue samples that can be evaluated according to the method 82 are described above. In one example, a tissue sample can be placed into the tissue chamber 18 by flow-loading (see Example 1). In another example, a tissue sample can be loaded into the feature side 12 of the microfluidic device 10 prior to coupling of the substrate 14 therewith.

At Step 88, at least one extrinsic stimulus can be applied to the tissue sample. The applied stimulus can be chemical, mechanical, or electrical in nature. A chemical stimulus can be applied to the tissue sample by perfusing a desired chemical (e.g., small molecule or pharmaceutical) or biological agent (e.g., growth factor, plasmid or transfection materials to modify cellular gene expression) through the system 60. A mechanical stimulus can be applied by manipulating the deformable membrane 44 (as described above) to impart a desired mechanical stress on the tissue sample. Additionally or optionally, a mechanical stimulus can be applied by operating the vacuum line(s) 56, as also described above, to impart a desired tensile stress on the tissue sample.

It will be appreciated that other ways of applying mechanical compression or tension to the tissue sample are also possible. For example, one or more prongs (not shown) could be disposed on the lower surface 50 of the deformable membrane 44. When the portion of the tissue chamber 18 behind the membrane 44 is pressurized, the membrane can bow into the tissue chamber and thereby cause the prong(s) to move away from each other and apply tension to the tissue sample. Also, applying compression to the tissue sample from the deflection of the membrane 44 can apply compression to some regions of the tissue sample and tension to other areas. Additionally, through the use of 3D imaging and image processing with labeled cell nuclei or vertices, the strain field that each cell comprising the tissue sample experiences can be measured to provide an idea of the extent of compression or tension, understand what region(s) is/are in compression and tension, and evaluate what is the unique biological response (or responses) to being in tension or compression. Other fluorescent biomarkers or biosensors can be designed or utilized to indicate changes in the mechanical microenvironment of the tissue sample.

Alternatively or additionally, the surface of a tissue sample can be decorated with microdroplets (e.g., of oil), or embedded therein, to provide a "stress sensor". Droplets can then be imaged to evaluate dilation or expansion of the droplet, which provides insight into the stress state. See, for example, Campas, O. et al., *Nature Methods*, 11(2):183-189 (2014).

In some instances, an electrical stimulus can be additionally or optionally be applied by delivering electrical energy to the first and second electrodes 38 and 40 to create an electrical gradient across the tissue chamber 18. For example, biosensors to measure changes in membrane voltages of cells can be used. These biosensors can be genetically encoded (see, for example, Han Z. et al., *PLoS ONE*. 2013 Nov. 27; 8(11):e81295.) or externally applied fluorescent (see, for example, Krüger J. et al., *BMC Dev Biol*. 2015; 15(1):1. PMCID: PMC4302609) or chemiluminescent dyes.

The central acquisition and control module 64 can automatically control application of the stimulus (or stimuli) to the tissue sample based, for example, on a preprogrammed protocol. In some instances, only a single stimulus can be applied to the tissue sample. In other instances, multiple stimuli can be applied to a tissue sample according to a scheduled plan (e.g., in series or simultaneously). Further, where the system 60 includes an array 36 with multiple tissue samples associated therewith, different stimuli can be separately applied to each of the tissues samples according to a preprogrammed protocol. Advantageously, each stimuli variable can be designed to elicit a specific physiological or supra-physiological response (e.g., indicated by the presence, absence, and/or concentration of detectable molecules, such as fluorescent reporters) from the tissue sample according to a preprogrammed experimental protocol, which, in turn, provides a controlled microenvironment that enables systematic investigation into the response of a developing or growing tissue sample.

At Step 90, data resulting from the applied extrinsic stimulus (or stimuli) can be obtained by imaging the tissue sample with the imaging modality 66. In some instances, such data can correspond to, or be indicative of, the presence, absence, and/or concentration of detectable molecules (e.g., fluorescent reporters) associated with one or more cells that comprise the tissue sample and which have had a stimulus (or stimuli) applied thereto. Image data can be automatically recorded and/or processed by the central acquisition and control module 64 to obtain a plurality of image data sets. Tensile stress, for example, can be spatially mapped to highlight regions of extreme and minimal tensile stresses, which is useful for ascertaining the mechanical state of individual cells. Once the central acquisition and control module 64 has recorded and/or processed the image data, the computational software associated therewith can co-register multiple imaging datasets. The generated data can then be evaluated (Step 92) to investigate the response of the tissue sample to the applied stimulus (or stimuli). For example, the image data associated with a particular biological response (to a stimulus) can be quantified. This information then can be used to modulate the stimulus (or stimuli) in a continuous fashion. The method 82 thus provides an unprecedented level of feedback control as compared to conventional methods, which are discontinuous, non-feedback processes requiring an experiment to be run, a response observed, and then a new experiment run with inputs that have been modified by the observed response.

Advantageously, the ability to study multiple tissue samples with uniquely addressable channels to modulate multiple external stimuli in a highly controlled environment permits an unprecedented level of experimental control in exploring the nexus of physiology and genetics associated with cellular tissue differentiation, morphogenesis, and cellular or tissue (e.g., organ) growth and development.

After completing the method 82, the system 60 (e.g., the microfluidic device(s) 10) can be disassembled and the tissues sample(s) recovered for further applications, including transplantation into the same or different subject, the generation of new cell lines, etc.

It will be appreciated that certain aspects of the present disclosure can find application in a variety of biomedical research and clinical treatment settings including, but not limited to:

tumor biopsy analysis—there are many open questions regarding the local chemical, mechanical, and electrical microenvironment and their effect(s) on cancer progression. The present disclosure can serve as a research tool to address such questions as it provides a model microenvironment that can be easily modified to test varying physiological and supra-physiological stimuli during ex vivo culture. For example, depending upon a detected change in mitosis to chemical, mechanical, and/or electrical factors, a cancer treatment plan can be formulated;

fluid mechanics analysis—aspects of the present disclosure can find use in studying the basic fluid mechanics of laminar flows around objects of different geometries. For example, structures can be placed in the tissue chamber 18 and the fluid inlet and outlet channels 20 and 22 can be used to perfuse fluids with suspended fluorescent microparticles. The walls 24 of individual tissue chambers 18 can be actuated to investigate flow regime changes as a response to varying boundary conditions. The electrical channels can be used to drive elecrokinetic flows or to sense ion transport in the tissue chambers 18;

cell culture and manipulation—aspects of the present disclosure can find use in stem cell culture or organ-like cultures derived from stem cells when exogenous stimuli, such as perfusion, mechanical forces, and/or electrical gradients are important for the growth, differentiation and homeostasis of the organ systems. Additionally, aspects of the present disclosure can be used to independently address exogenous stimuli, in single or combination, for the differentiation, dedifferentiation, or reprogramming of cells into other cell types;

patient-specific invasion assays—tissue biopsies can be subdivided and placed into different tissue chambers 18 and then perfused with different drugs. Different assays and readouts, such as transfected live-imaging fluorescent or bioluminescent reporters can be collected to ascertain the effects of specific drugs or combinations of drugs on cell function and viability within the biopsy (which may contain both normal and diseased cells or tumors) that can be used to predict the efficacy of the drug cocktail for that particular patient; and systems-level analysis of tissue microarchitecture—aspects of the present disclosure can be combined with the microfluidic devices, systems, and method disclosed in U.S. patent application Ser. No. 14/737,986, filed Jun. 12, 2015, to provide systems-level information of the tissue microarchitecture for individuals. The large image datasets (4D and 5D) can be combined with patient-specific RNA-seq, microarray, preoteomic and/or DNA sequencing to relate such "big data" sets with the spatio- and temporal organization of cells within a given tissue type. This imaging data can therefore vastly expand the knowledge of how DNA affects subtle phenotypes, such as changes in the microarchitecture of tissues. For a company or health care provider that has access to multiple diverse data types, this may produce additional benefits regarding the future susceptibility of patients to disease or other conditions based on the combined information from spatial imaging of the biopsies with DNA sequencing, etc. This additional benefit may also be useful for predicting health outcomes for currently healthy subjects.

The following examples are for the purpose of illustration only and are not intended to limit the scope of the appended claims.

Example 1

This Example describes the evaluation, according to certain aspects of the present disclosure, of a $3^{rd}$ instar *Drosophila* wing imaginal disc, representative of an organ system, being cultured in WM1 media (Zartman et al., 2013) under a spinning disc confocal microscope.

WM1 media was formulated as follows: Schneider's *Drosophila* Media (base) (from Gibco, 1×, 500 mL); heat inactivated fly extract (ground-up and filtered flies); 6.2 µg/mL human insulin from a 1 mg/mL stock aliquot diluted in PBS (stock aliquot prepared from Sigma Aldrich, 9.5-11.5 mg/mL human insulin (chemically defined, recombinant from *Saccharomyces cerevisiae*, sterile-filtered, BioXtra); and 1:200 Penicillin-Streptomycin (from Gibco, Penicillin-Streptomycin (10,000 U/mL).

Imaging was performed on a Nikon Eclipse Ti confocal microscope (Nikon Instruments Inc., Melville, N.Y.) with a Yokogawa spinning disc and MicroPoint laser ablation system (Andor Technology, South Windsor, Conn.). Image data were collected on an iXonEM+ cooled CCD camera (Andor Technology, South Windsor, Conn.) using MetaMorph® v7.7.9 software (Molecular Devices, Sunnyvale, Calif.). All experiments were performed immediately following dissection to minimize time in culture. $3^{rd}$ instar larvae were picked from sides of culture vial with forceps and washed in a 35 mm Petri dish filled with 70% isopropyl alcohol (IPA) for 60 seconds. Larvae were transferred with forceps to a different Petri dish filled with PBT (0.03% Triton X-100 diluted in PBS). Larvae were stored in this mixture while awaiting dissection (variable times). Larvae were dissected in WM1 media (Zartman J. et al., Development 2013; 140(3):667-74) and flow-loaded into an imaging chamber as shown in FIGS. 8A-D.

Figure 9A:
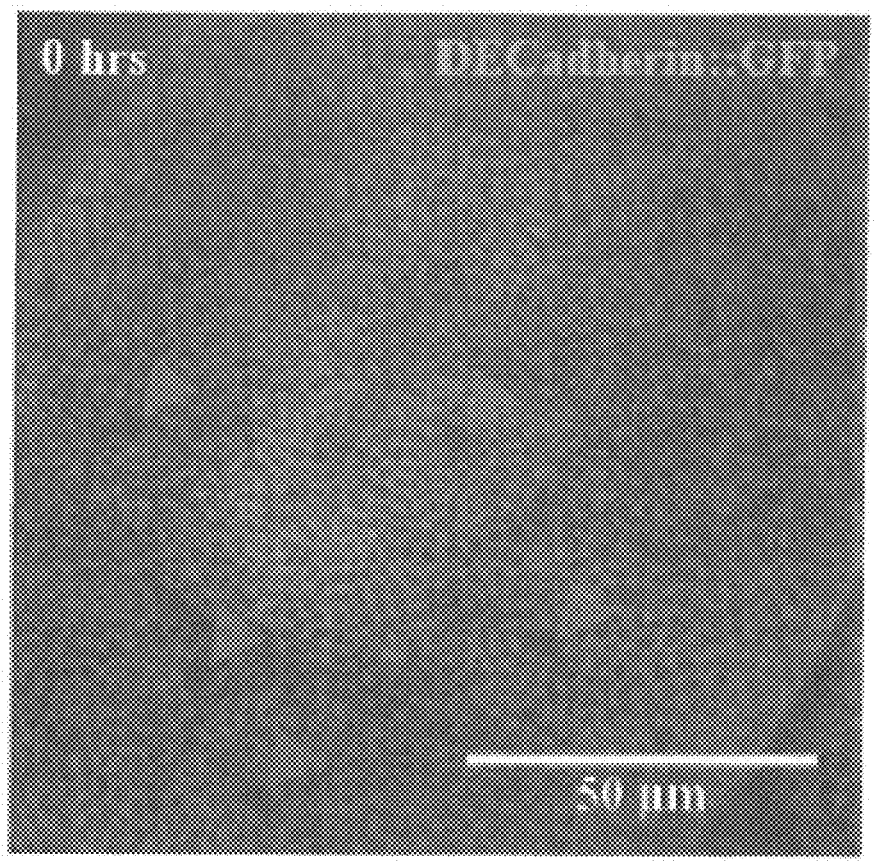
FIGS. 9A-B are images showing the results of Example 1 (a maximum projection at the time point specified in the upper left of each image. Original data represents a z-stack of 53 μm depth, imaged at 1 μm intervals (53 "z-slices") with an exposure time of 300 ms/slice. Red arrows mark mitotic (live) cells in each image)
Figure 9B:
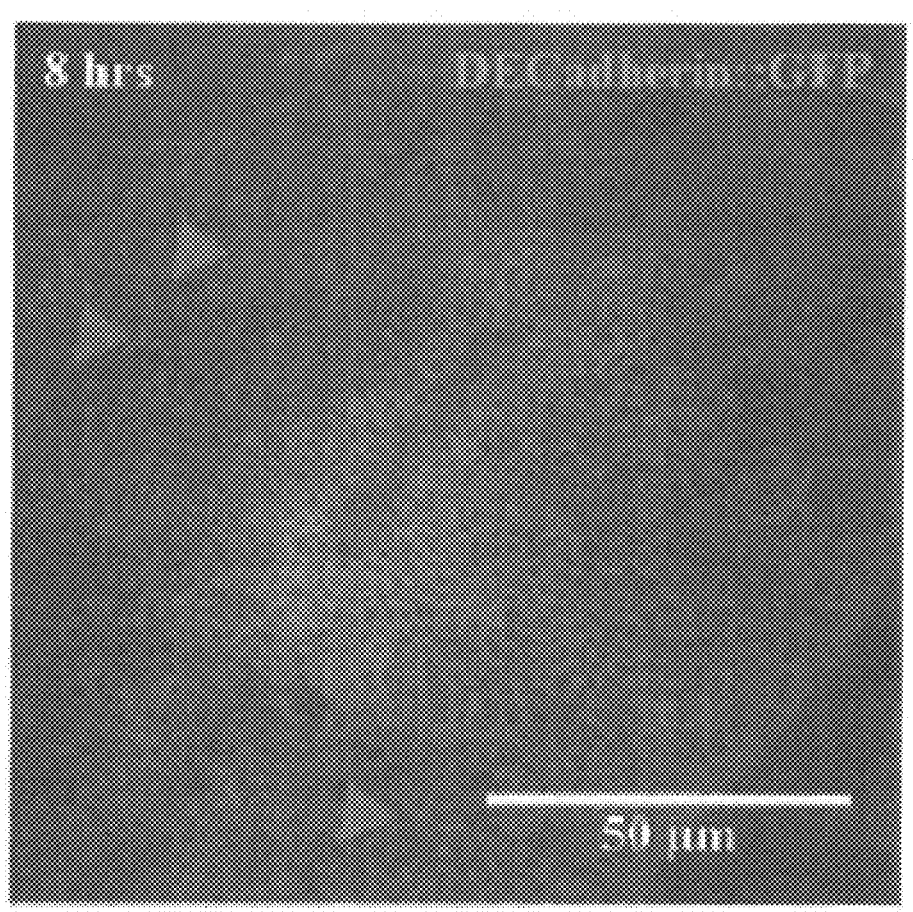

WM1 media was flowed through the imaging chamber at a flow rate of 2 µl/hr and then imaged as described above. The temporal imaging interval was 15 minutes. Imaging was done at 488 nm (GFP), 60× magnification, and 300 ms exposure time. FIGS. 9A-B shown a maximum projection at the time point specified in the upper left of each image. Original data represents a z-stack of 53 µm depth, imaged at 1 µm intervals (53 "z-slices") with an exposure time of 300 ms/slice. Red arrows mark mitotic (live) cells in each image.

Example 2

This example describes an experiment evaluating the effects of mechanical deformation on a $3^{rd}$ instar *Drosophila* wing imaginal disc.

Figure 10:
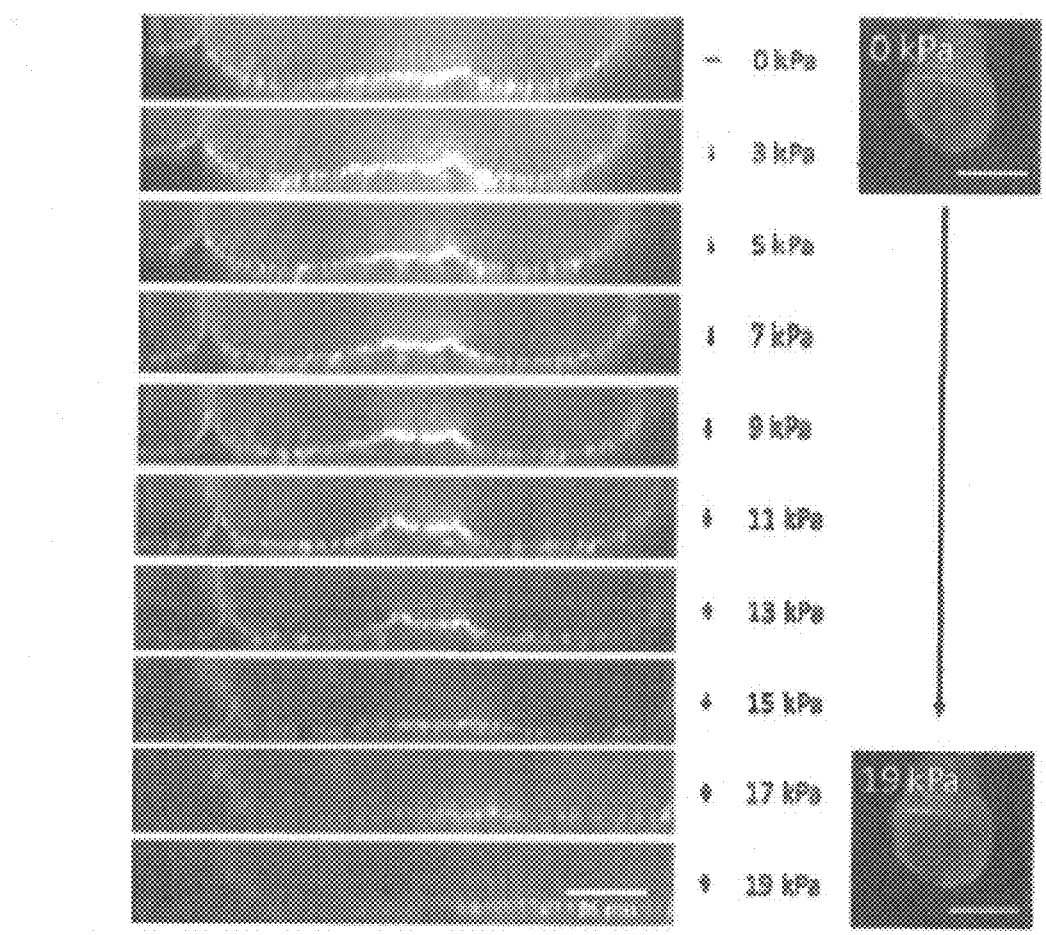
FIG. 10 is a series of images showing the effects of mechanical deformation on a $3^{rd}$ instar *Drosophila* wing imaginal disc.

A $3^{rd}$ instar *Drosophila* wing imaginal disc was dissected and loaded as described in Example 1. As shown in FIG. 10, a single z-stack was imaged at each applied pressure before pressure was manually increased to the next value. Data represent a z-stack of 57 µm depth, imaged at 1 µm intervals (57 "z-slices") with an exposure time of 300 ms/slice. Images at the far left of FIG. 10 show an orthogonal view through the wing disc pouch at the red, dashed line in the small inset images at right. FIG. 11 is a graph showing the results of Example 2.

From the above description of the present disclosure, those skilled in the art will perceive improvements, changes and modifications. For example, although the term "microfluidic" is used herein, it will be understood that the dimensions of any device, structure, or component associated with the term will not be limited to the micro-scale. Rather, the term "microfluidic" can refer to devices, systems, and/or components of the present disclosure configured to handle small volumes of liquids or fluids and, moreover, that any device, structure, or component associated with the term can have dimensions greater or less than the micro-scale. Such improvements, changes, and modifications are within the skill of those in the art and are intended to be covered by the appended claims. All patents, patent applications, and publication cited herein are incorporated by reference in their entirety.

The following is claimed:

1. A microfluidic device for evaluating a tissue sample, the device comprising:
   a tissue chamber defined by
      a deformable membrane oppositely disposed from a transparent wall, the deformable membrane that oscillates, upon application of pressure thereto, to mechanically compress the tissue sample,
      at least one deformable wall, the deformable wall extending perpendicularly between the deformable membrane and the transparent wall, the deformable stretching either uniaxially or biaxially upon application of negative pressure to the tissue chamber;
   a liquid inlet channel in fluid communication with the tissue chamber;
   a liquid outlet channel in fluid communication with the tissue chamber; and
   first and second electrodes oppositely disposed about the tissue chamber to deliver electrical energy to and create an electrical gradient across the tissue chamber.

2. The device of claim 1, further including at least one pressure line in fluid communication with the tissue chamber.

3. The device of claim 2, further including at least one vacuum line, the vacuum line abutting a corresponding deformable wall, the vacuum line applying pressure to the corresponding deformable wall to cause the corresponding deformable wall to stretch.

4. The device of claim 1, wherein an interior surface of the liquid inlet channel is textured to induce local turbulence in a liquid flowing therethrough.

5. The device of claim 1, further comprising at least one piezoelectric element connected to an outer surface of the transparent wall such that delivery of an oscillatory voltage to the piezoelectric element induces a vibration that propagates through the transparent wall into the tissue sample.

6. The device of claim 1, further including a microwave connected thereto.

7. The device of claim 1, wherein the tissue sample is a growing organ or a tissue explant.

8. The device of claim 1, wherein the tissue chamber is substantially circular.

9. The device of claim 1, further including a transparent substrate, the transparent substrate having a first major surface, the tissue chamber, the liquid inlet channel, the liquid outlet channel, and the first and second electrodes being coupled to the first major surface of the transparent substrate, the transparent wall of the tissue chamber comprising a portion of the first major surface of the transparent substrate.

10. The device of claim 1, wherein the first and second electrodes are indirectly coupled to the liquid inlet channel and the liquid outlet channel, respectively, the first and second electrodes being located atop respective plugs, which prevent the escape of a liquid from the liquid inlet channel and the liquid outlet channel, respectively.

* * * * *